United States Patent [19]

Hugo et al.

[11] Patent Number: 4,599,425
[45] Date of Patent: Jul. 8, 1986

[54] BIS-[2,5-DITHIO-1,3,4-THIADIAZOLE] AND A PROCESS FOR ITS PRODUCTION

[75] Inventors: Peter Hugo; Rainer Noack, both of Berlin, Fed. Rep. of Germany

[73] Assignee: Rhein-Chemie Rheinau GmbH, Mannheim, Fed. Rep. of Germany

[21] Appl. No.: 662,141

[22] Filed: Oct. 18, 1984

Related U.S. Application Data

[63] Continuation-in-part of Ser. No. 640,618, Aug. 14, 1984, abandoned.

[30] Foreign Application Priority Data

Aug. 27, 1983 [DE] Fed. Rep. of Germany ....... 3330919

[51] Int. Cl.⁴ ............................................ C07D 513/18
[52] U.S. Cl. .................................................... 548/142
[58] Field of Search .......................................... 548/142

[56] References Cited

U.S. PATENT DOCUMENTS 3,725,362 4/1973 Walker .

FOREIGN PATENT DOCUMENTS 1078538 8/1967 United Kingdom .

Primary Examiner—Robert Gerstl
Attorney, Agent, or Firm—Connolly and Hutz

[57] ABSTRACT

Bis-[2,5-dithio-1,3,4-thiadiazole] corresponding to the following formula:

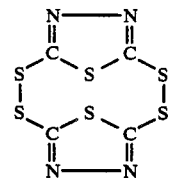

is obtained by reacting 2,5-dimercapto-1,3,4-thiadiazole and hydrogen peroxide in the absence of other reactants.

4 Claims, No Drawings

BIS-[2,5-DITHIO-1,3,4-THIADIAZOLE] AND A PROCESS FOR ITS PRODUCTION

This application is a continuation in part of Ser. No. 640,618 filed Aug. 14, 1984, now abandoned.

This invention relates to bis-[2,5-dithio-1,3,4-thiadiazole], hereinafter referred to as BDTD, and to a process for producing BDTD from 2,5-dimercapto-1,3,4-thiadiazole, hereinafter referred to as DMTD, and hydrogen peroxide.

BDTD is a valuable intermediate product for the production of oil-soluble, corrosion-inhibiting additives.

For example, BDTD can be reacted with a tertiary hydrocarbylmercaptan with 4 to 60 carbon atoms at a temperature of from 20° to 150° C. and with a molar ratio of the reactants of 1:2 to produce 2 (hydrocarbyl-dithio)-5-mercapto-1,3,4-thiadiazole, a known corrosion inhibitor (U.S. Pat. No. 3,663,561).

The production of the starting material, DMTD, is known from Ber. 27, 2507 (1894) and DE-PS No. 81,437.

Oxidation reactions involving DMTD have already been described in the literature. E. Ziegele, J. Prakt. Chem. 60, 40 (1899) oxidizes alcohole solutions of DMTD with iodine or iron-(III) chloride. In both cases, he identified the following compound:

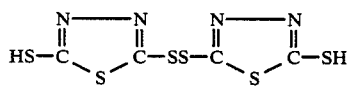

Also, an insoluble residue is formed with iron-(III) chloride, probably corresponding to the following formula:

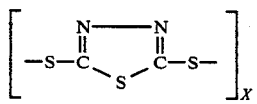

where X represents an unknown degree of polymerization.

S. M. Losanitch in Soc. 121, 1542 (1923) carries out the oxidation of an alcoholic solution of DMTD with an excess of iodine. He obtains a compound which he states is not identical with the poly compound obtained by Ziegele, l.c., and which, according to elemental analysis, has the composition $C_4H_4N_4S_7$.

Hitherto, the oxidation of DMTD with $H_2O_2$ has only ever been carried out in the presence of other reactants. More particularly, U.S. Pat. Nos. 3,087,932 and 3,663,561 describe processes in which oil-soluble derivatives of DMTD are directly obtained by the simultaneous reaction of DMTD, hydrogen peroxide and mercaptans. Unfortunately, these products are not homogeneous and, in some cases, they require subsequent working up.

The object of the present invention is to produce BDTD.

According to the invention, this object is achieved by reacting DMTD and hydrogen peroxide in the absence of other reactants at a temperature of up to 100° C. and preferably at a temperature in the range from 20° to 50° C. DMTD is preferably used in the form of a suspension in water because DMTD is only sparingly soluble in water (approximately 10 g/l at 20° C.). The molar ratio of DMTD to $H_2O_2$ is preferably 1:1. BDTD is obtained without any troublesome secondary products.

Another advantage lies in the fact that the reaction mixture accumulating in the production of DMTD in accordance with DE-PS No. 958,650 may be directly further processed into BDTD, i.e. without having to be isolated beforehand, by the process according to the present invention. This avoids losses through isolation of the DMTD.

BDTD is obtained in a substantially quantitative yield in the form of a substantially colorless deposit which is insoluble in the reaction solution. Elemental analysis of the washed and dried deposit indicates an atomic ratio C:N:S of 2:2:3. Analysis by mass spectroscopy reveals the molecular weight of 296 typical of BDTD and the fragments to be expected from its structural formula. Other physical molecular weight determinations are impossible on account of the insolubility of BDTD in all the usual solvents.

EXAMPLE 1

15 g of DMTD (0.1 mole) in the form of a powder having a particle diameter of less than 0.5 mm were suspended in 200 ml of water at 20° C. 12 g of 35% hydrogen peroxide solution (corresponding to 0.1 mole) were then added with vigorous stirring at such a rate that the reaction temperature did not exceed 50° C. 1 hour after addition of the hydrogen peroxide, the resulting BDTD was filtered off and dried. At 15 g (0.05 mole) the yield was quantitative.

EXAMPLE 2

50 g (1 mole) of hydrazine hydrate and 120 g (3 moles) of sodium hydroxide in 500 ml of water were initially introduced into the reaction vessel. 152 g (2 moles) of carbon disulfide were then added with cooling and vigorous stirring at such a rate that the reaction temperature did not exceed 40° C. After stirring for 3 hours at 40° C., the DMTD was precipitated by the addition of 300 g (3 moles) of 35% hydrochloric acid, hydrogen sulfide being evolved at the same time. The hydrogen sulfide was completely driven out by gassing with nitrogen. 120 g of 35% hydrogen peroxide solution (1 mole) were added with vigorous stirring to the reaction mixture accumulating at such a rate that the reaction solution did not exceed 50° C. 1 hour after addition of the hydrogen peroxide, BDTD was filtered off, washed repeatedly with water and dried. The yield of BDTD amounted to 140 g, corresponding to 93% of the theoretical yield, based on carbon disulfide and hydrazine hydrate.

EXAMPLE 3

40 g (0.2 mole) of tert.-dodecyl mercaptan and 30 g (0.1 mole) of powdered BDTD were stirred at room temperature to form a paste. The mixture thus prepared was then left standing for 2 hours at 100° C. in a drying cabinet. A weight check before and after the reaction in the drying cabinet did not reveal any measurable weight loss.

The yellow, viscous liquid product obtained after cooling at room temperature was analyzed by high pressure liquid chromatography and showed 98 mole % of 2-(tert.-dodecyldithio)-5-mercapto-1,3,4-thiadiazole and 2 mole % of tert.-dodecylmercaptan.

In addition, an osometric molecular weight determination was carried out and, at M=346 g/mole, produced virtually the theoretrical value (350.6 g/mole).

We claim:

1. Bis-[2,5-dithio-1,3,4-thiadiazole] corresponding to the following formula:

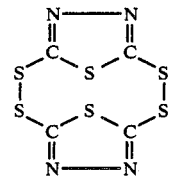

2. A process for producing the compound claimed in claim 1, characterized in that 2,5-dimercapto-1,3,4-thiadiazole in water is reacted with hydrogen peroxide in the absence of other reactants at a temperature of up to 100° C. wherein the molar ratio of 2,5-dimercapto-1,3,4-thiadiazole to hydrogen peroxide is 1:1.

3. A process as claimed in claim 2, characterized in that 2,5-dimercapto-1,3,4-thiadiazole is intially introduced in the form of a suspension in water, followed by the addition of hydrogen peroxide or an aqueous solution of hydrogen peroxide.

4. A process as claimed in claim 2, characterized in that the molar ratio of 2,5-dimercapto-1,3,4-thiadiazole to $H_2O_2$ is 1:1 and the reaction temperature is in the range from 20° to 50° C.

* * * * *